United States Patent
Okumura et al.

(10) Patent No.: US 10,684,254 B2
(45) Date of Patent: Jun. 16, 2020

(54) ANALYTE DETECTION BY DIELECTROPHORESIS

(71) Applicant: Panasonic Intellectual Property Management Co., Ltd., Osaka (JP)

(72) Inventors: Yasuaki Okumura, Kyoto (JP); Tatsurou Kawamura, Kyoto (JP); Noriko Shimba, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 311 days.

(21) Appl. No.: 15/366,143

(22) Filed: Dec. 1, 2016

(65) Prior Publication Data

US 2017/0227492 A1    Aug. 10, 2017

(51) Int. Cl.
| | |
|---|---|
| *G01N 27/447* | (2006.01) |
| *B03C 5/00* | (2006.01) |
| *G01N 33/543* | (2006.01) |

(52) U.S. Cl.
CPC ....... *G01N 27/44726* (2013.01); *B03C 5/005* (2013.01); *G01N 33/5438* (2013.01)

(58) Field of Classification Search
CPC .......... G01N 27/44726; G01N 33/5438; B01L 2200/06–0694; B01L 2400/0406–0427; B01F 13/0001–001; B03C 5/00–028
See application file for complete search history.

(56) References Cited

U.S. PATENT DOCUMENTS

| | | | |
|---|---|---|---|
| 6,790,330 B2* | 9/2004 | Gascoyne | B03C 5/026 204/547 |
| 2002/0155586 A1* | 10/2002 | Cheng | B01D 57/02 435/287.1 |

(Continued)

FOREIGN PATENT DOCUMENTS

| | | |
|---|---|---|
| JP | 61-272663 | 12/1986 |
| JP | 4-080657 | 3/1992 |
| JP | 11-127846 | 5/1999 |

OTHER PUBLICATIONS

H. J. Lee, et al., Rapid and simple immunosensing system for simultaneous detection of tumor markers based on negative-dielectrophoretic manipulation of microparticles, Talanta, vol. 81, pp. 657-663 (2010) (Year: 2010).*

*Primary Examiner* — Maris R Kessel
(74) *Attorney, Agent, or Firm* — McDermott Will & Emery LLP (57) ABSTRACT

The present invention provides a method for detecting an analyte with high sensitivity. In the present method, a solution is supplied onto a substrate comprising a first electrode and a second electrode. Then, an alternating voltage is applied between the first electrode and the second electrode to aggregate, onto the surface between the first electrode and the second electrode by dielectrophoresis, bioparticles and dielectric particles contained in the solution. The aggregated bioparticles are broken to release the analyte contained in the bioparticles. The released analyte is bound to a first antibody and a second antibody to cause the dielectric particles to be immobilized onto the substrate through formation of a sandwich structure composed of the (Continued)

first antibody, the analyte, and the second antibody. Finally, the analyte is detected through the fluorescent substance contained in the immobilized dielectric particles.

2 Claims, 10 Drawing Sheets

(56) References Cited

U.S. PATENT DOCUMENTS

2003/0146100 A1* 8/2003 Huang ............... B01L 3/502761
  204/547
2009/0071831 A1* 3/2009 Chen ................... G01N 27/447
  204/547

* cited by examiner

ANALYTE DETECTION BY DIELECTROPHORESIS

BACKGROUND

1. Technical Field

The present invention relates to analyte detection by dielectrophoresis.

2. Description of the Related Art

Figure 8:
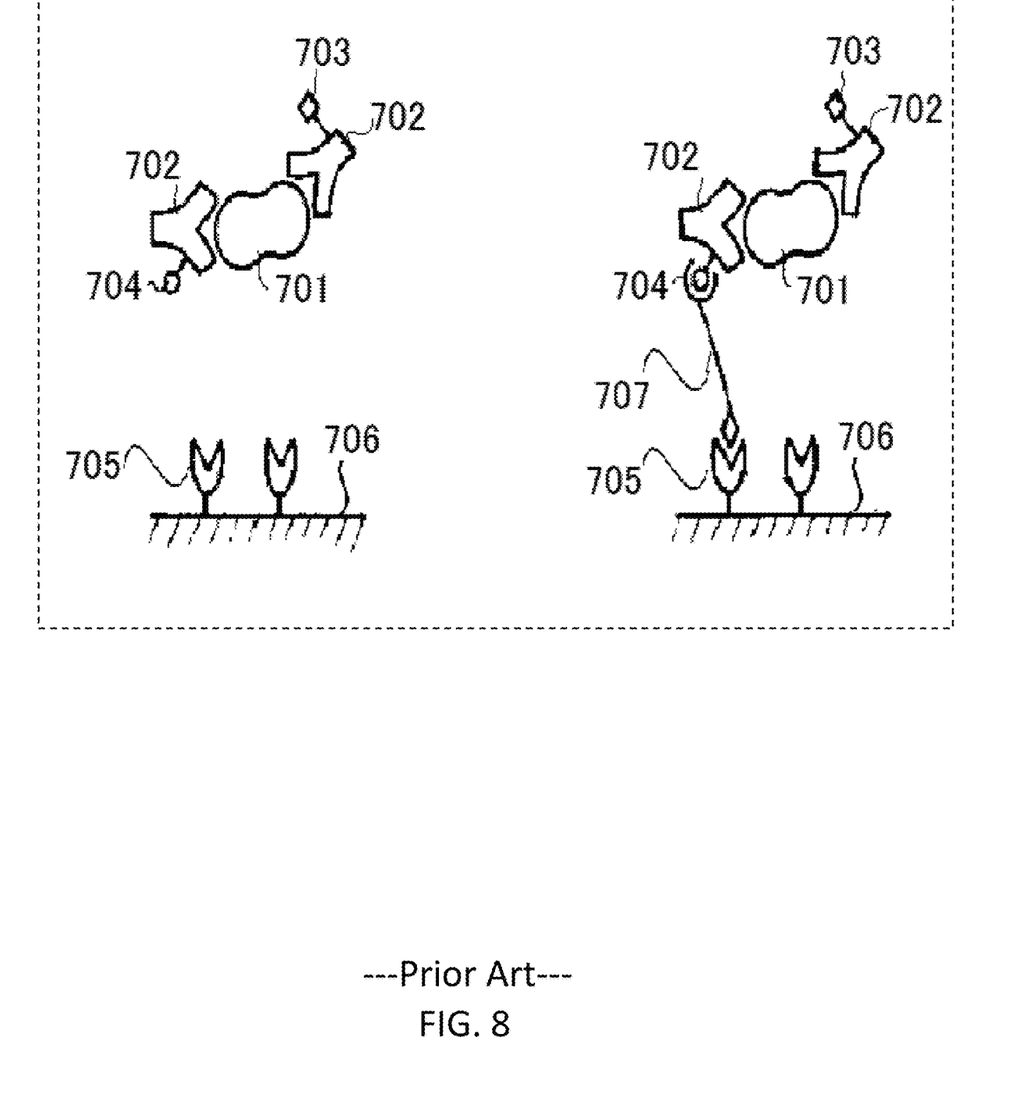
FIG. 8 is a duplicate of a part of FIG. 1 included in Japanese Patent laid-open Publication No. Hei 4-080657.

Japanese Patent laid-open Publication No. Hei 4-080657 discloses an immune measurement method and apparatus. FIG. 8 shows a duplicate of a part of FIG. 1 included in Japanese Patent laid-open Publication No. Hei 4-080657. The left drawing included in FIG. 8 shows a state where an analyte 701 contained in a sample solution forms a reaction product with an antibody (or antigen) 702 having a labeled substance 703 and a specific reaction material 704. The right drawing included in FIG. 8 shows a state where the reaction product is immobilized onto a solid phase 706 through an antibody 705 by adding an intermediary 707.

Figure 9:
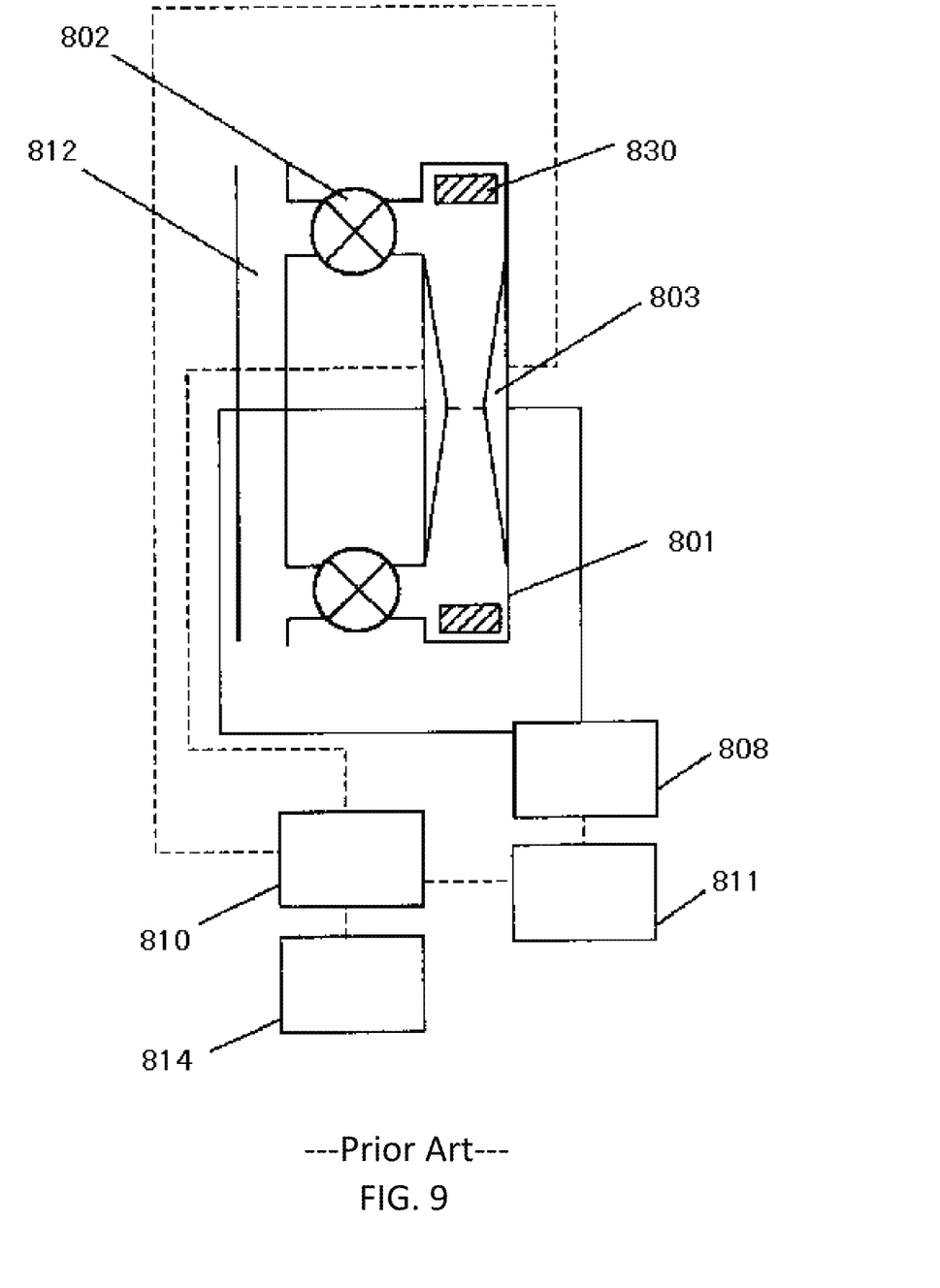
FIG. 9 is a duplicate of FIG. 1 included in Japanese Patent laid-open Publication No. Hei 11-127846.

Japanese Patent laid-open Publication No. Hei 11-127846 discloses an apparatus for measuring a microbial cell number and measurement of microbial cell number. FIG. 9 shows a duplicate of FIG. 1 included in Japanese Patent laid-open Publication No. Hei 11-127846. According to the front page thereof, this apparatus for measuring the microbial cell number is equipped with a cell 801 capable of introducing a microorganism-containing liquid and having plural electrodes 803 in the interior thereof, a power source circuit 808 capable of applying an AC current for causing the dielectric migration and a high-voltage pulse for destroying the microorganisms across the electrodes 803, a controlling means 811 for controlling the power source circuit 808 and a measuring means 810 capable of measuring physical properties of the liquid when the microorganisms are destroyed. The controlling means 811 is capable of flowing the AC current, making the microorganisms migrate to a prescribed position by the dielectric migration, applying the high-voltage pulse thereto and destroying the microorganisms and the measuring means 810 is capable of measuring the physical properties of the liquid after destroying the microorganisms and calculating the microbial cell number. Reference Signs 802, 812, and 814 indicate a valve, a sample solution, and a memory, respectively.

Figure 10:
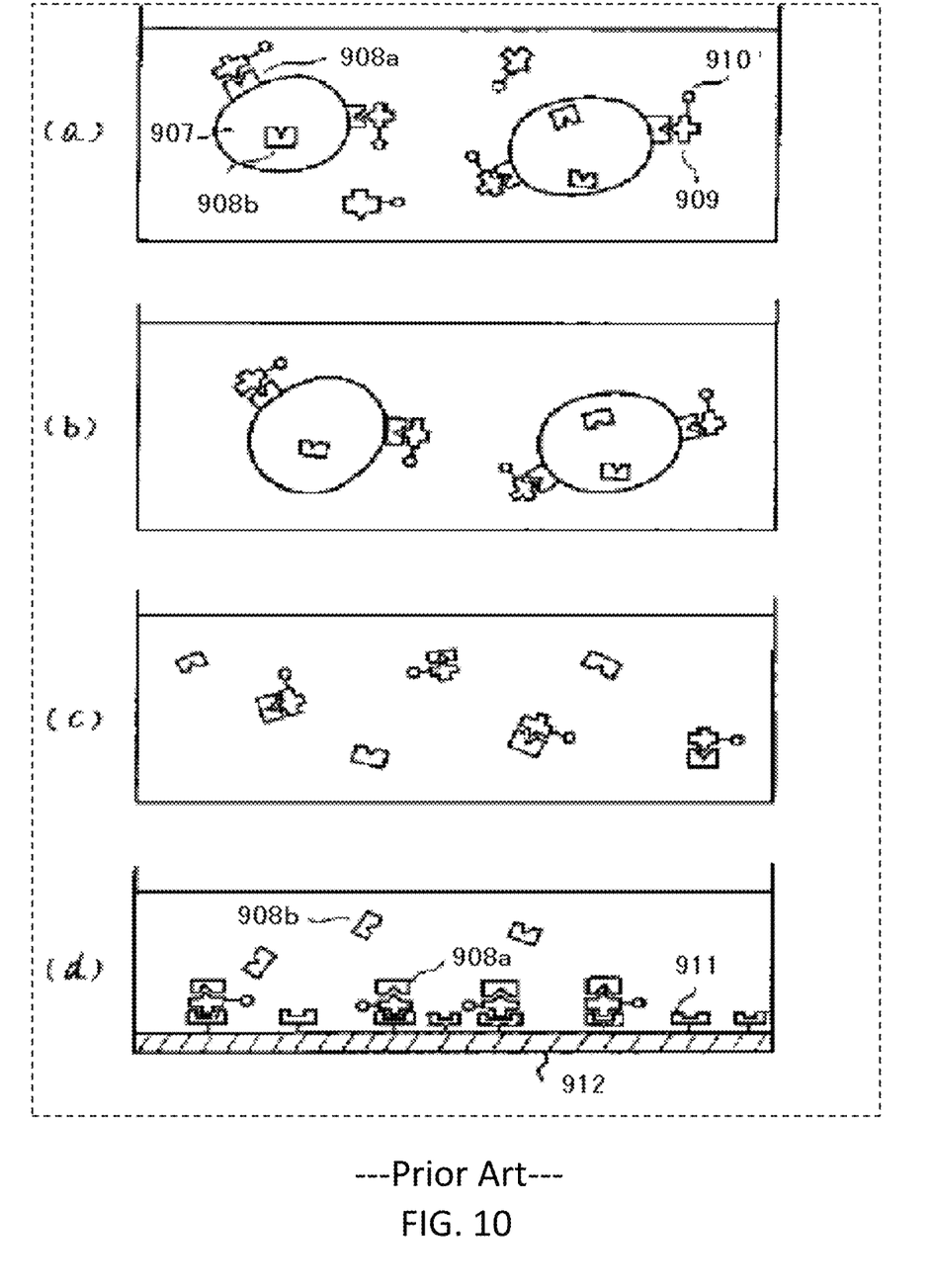
FIG. 10 is a duplicate of FIG. 2 included in Japanese Patent laid-open Publication No. Sho 61-272663.
Figure 11:
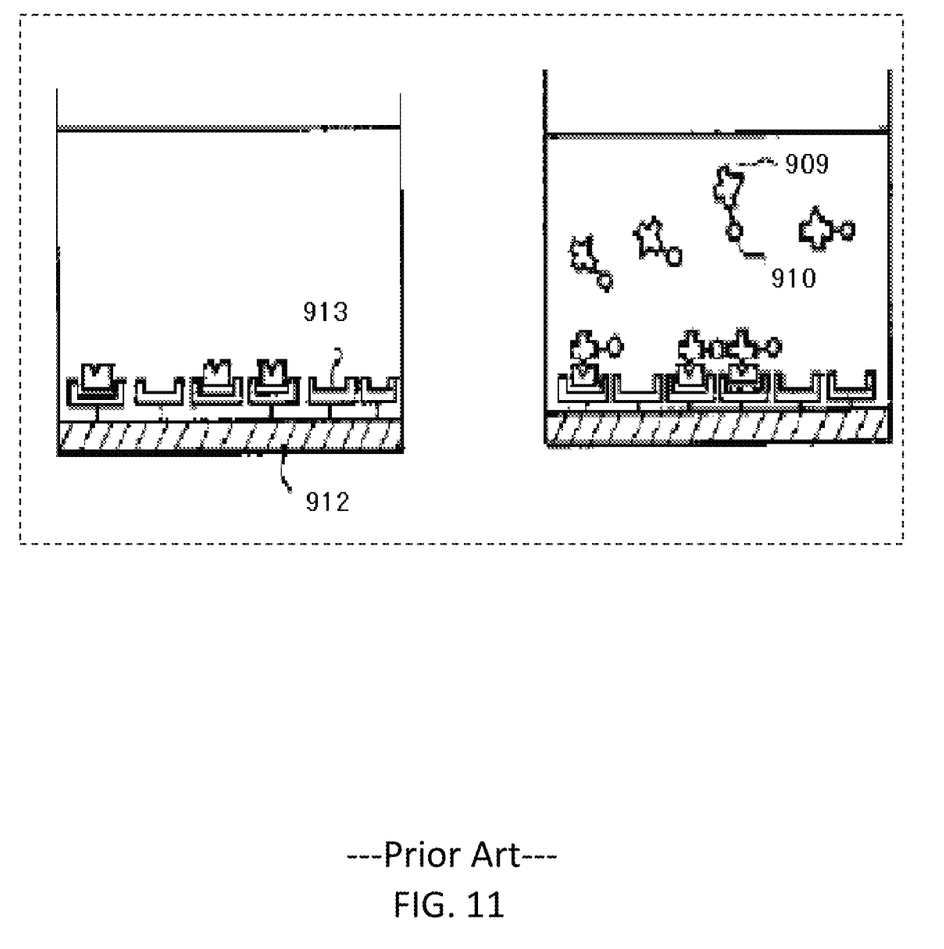
FIG. 11 is a duplicate of FIG. 4 included in Japanese Patent laid-open Publication No. Sho 61-272663.

Japanese Patent laid-open Publication No. Sho 61-272663 discloses a detection of a cancer-associated antigen. FIG. 10 and FIG. 11 are duplicates of FIG. 2 and FIG. 4 included in Japanese Patent laid-open Publication No. Sho 61-272663, respectively. As shown in the parts (b) and (c) of FIG. 10, cells 907 are broken with a blender to release CEA antigens 908b. As shown in the left part of FIG. 11, the CEA antigens 908b are bound to CEA antibodies 913 immobilized on a solid phase 912. The cell 907 has a CEA antigen 908a also on the surface thereof. An anti-CEA antibody 909 having a labeled substance 910 is bound to the CEA antigen 908a.

SUMMARY

An object of the present invention is to provide a method and a device for detecting an analyte with high sensitivity.

The present invention provides a method for detecting an analyte, the method comprising:

(a) supplying a solution onto a substrate comprising a first electrode and a second electrode;
wherein
the substrate has a first antibody on the surface thereof between the first electrode and the second electrode;
the solution contains dielectric particles and at least one kind of bioparticles selected from the group consisting of viruses and cells;
each of the dielectric particles has a second antibody on the surface thereof;
each of the dielectric particles contains a fluorescent substance;
each of the bioparticles contains the analyte;
the first antibody is capable of binding to the analyte; and
the second antibody is capable of binding to the analyte;
(b) applying an alternating voltage between the first electrode and the second electrode to aggregate the bioparticles and the dielectric particles onto the surface of the substrate between the first electrode and the second electrode by dielectrophoresis;
(c) breaking the bioparticles aggregated in the step (b) to release the analyte contained in the bioparticles;
wherein
the released analyte is bound to the first antibody and the second antibody to cause the dielectric particles to be immobilized onto the substrate through formation of a sandwich structure composed of the first antibody, the analyte, and the second antibody;
and
(d) detecting the analyte through the fluorescent substance contained in the immobilized dielectric particles.

The present invention also provides a method for detecting an analyte, the method comprising:

(a) supplying a solution to a flow path formed between a substrate comprising a first electrode and a cover comprising a second electrode;
wherein
the substrate has a first antibody on the surface thereof near the first electrode;
the solution contains dielectric particles and at least one kind of bioparticles selected from the group consisting of viruses and cells;
each of the dielectric particles has a second antibody on the surface thereof;
each of the dielectric particles contains a fluorescent substance;
each of the bioparticles contains the analyte;
the first antibody is capable of binding to the analyte; and
the second antibody is capable of binding to the analyte;
(b) applying an alternating voltage between the first electrode and the second electrode to aggregate the bioparticles and the dielectric particles onto the surface of the substrate near the first electrode by dielectrophoresis;
(c) breaking the bioparticles aggregated in the step (b) to release the analyte contained in the bioparticles;
wherein
the released analyte is bound to the first antibody and the second antibody to cause the dielectric particles to be immobilized onto the substrate through formation of a sandwich structure composed of the first antibody, the analyte, and the second antibody; and
(d) detecting the analyte through the fluorescent substance contained in the immobilized dielectric particles.

The present invention also includes a device used for the above methods.

The present invention provides a method and a device for detecting an analyte with high sensitivity.

DETAILED DESCRIPTION OF THE EMBODIMENTS

Hereinafter, embodiments of the present invention will be described with reference to the drawings.

First Embodiment (Step (a))

Figure 1:
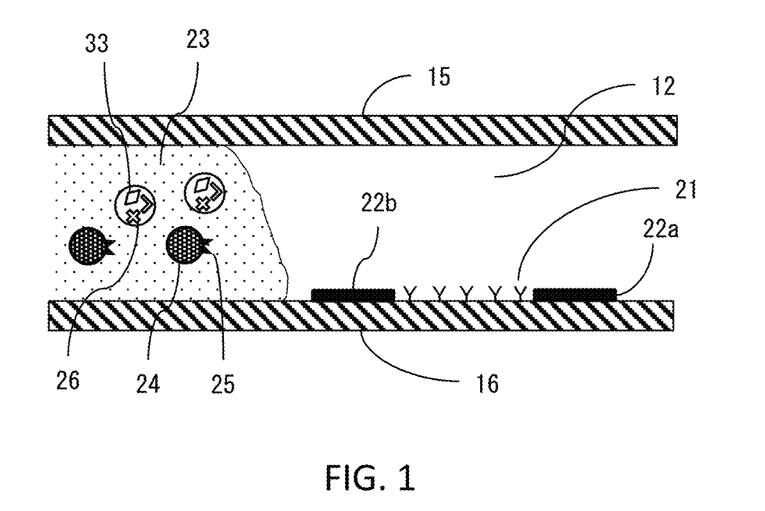
FIG. 1 shows a schematic view of a step (a) included in a method according to a first embodiment of the present invention.

First, as shown in FIG. 1, a solution 23 is supplied onto a substrate 16 comprising a first electrode 22a and a second electrode 22b on the surface thereof. A flow path 12 is formed between the substrate 16 and a cover 15. The solution 23 flows through the flow path 12. The cover 15 need not be provided.

The substrate 16 has first antibodies 21 on the surface thereof between the first electrode 22a and the second electrode 22b. The solution 23 contains at least one kind of bioparticles 26 selected from the group consisting of viruses and cells. The solution 23 contains dielectric particles 24. Desirably, the solution 23 is an aqueous solution.

Each of the dielectric particles 24 has second antibodies 25 on the surface thereof. Each of the dielectric particles 24 contains a fluorescent substance (not shown). Specifically, the dielectric particles 24 may have the fluorescent substance on the surface thereof; however, it is desirable that the dielectric particles 24 contain the fluorescent substance.

Each of the bioparticles 26 contains an analyte 33. An example of the analyte is a protein, a nucleic acid, or a sugar chain.

The first antibody 21 is capable of binding to the analyte 33. The second antibody 25 is also capable of binding to the analyte 33. It is desirable that a part of the analyte 33 to be bound to the first antibody 21 is different from a part of the analyte 33 to be bound to the second antibody 25. In other words, it is desirable that the analyte 33 comprises a first epitope and a second epitope (both of which are not shown) to be bound to the first antibody 21 and the second antibody 25, respectively.

(Step (b))

The step (b) is conducted after the step (a).

Figure 2:
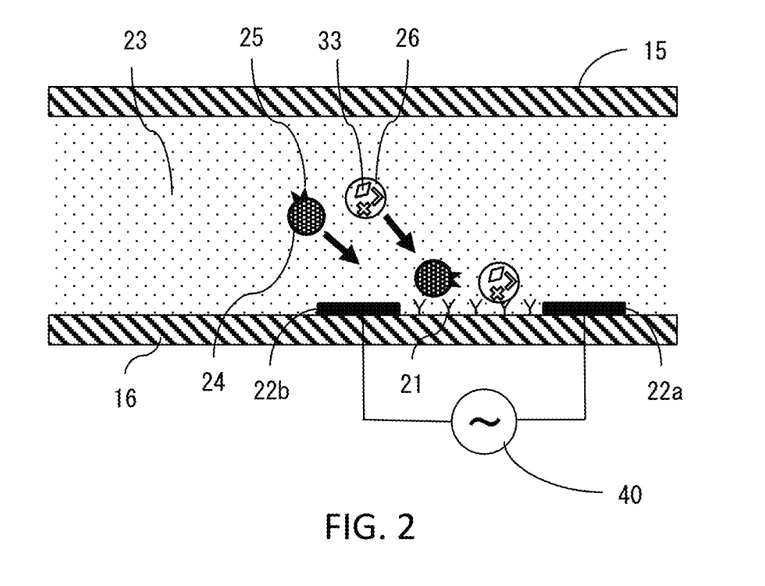
FIG. 2 shows, subsequently to FIG. 1, a schematic view of a step (b) included in the method according to the first embodiment.

As shown in FIG. 2, after the flow path 12 is filled with the solution 23, an alternating voltage is applied between the first electrode 22a and the second electrode 22b from an alternating-current power supply 40. An example of the applied alternating voltage and its frequency are 1 Vpp-20 Vpp and 0.1 MHz-1 MHz, respectively.

Figure 3:
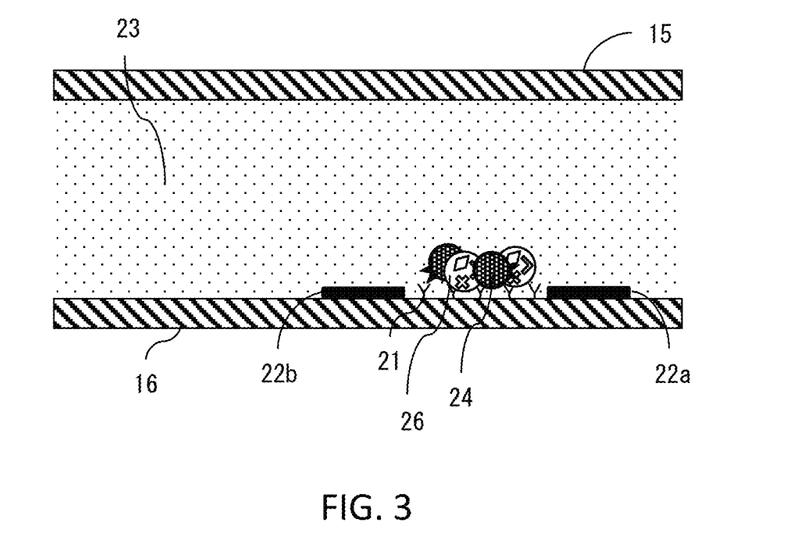
FIG. 3 shows a schematic view after completion of the step (b).

In this way, the bioparticles 26 and the dielectric particles 24 aggregate onto the surface of the substrate 16 between the first electrode 22a and the second electrode 22b by dielectrophoresis. As a result, the bioparticles 26 and the dielectric particles 24, both of which have been dispersed in the solution 23, are located with high density on the surface of the substrate 16 between the first electrode 22a and the second electrode 22b. As just described, as shown in FIG. 3, the bioparticles 26 and the dielectric particles 24 are located with high density by dielectrophoresis.

(Step (c))

The step (c) is conducted after the step (b).

Figure 4:
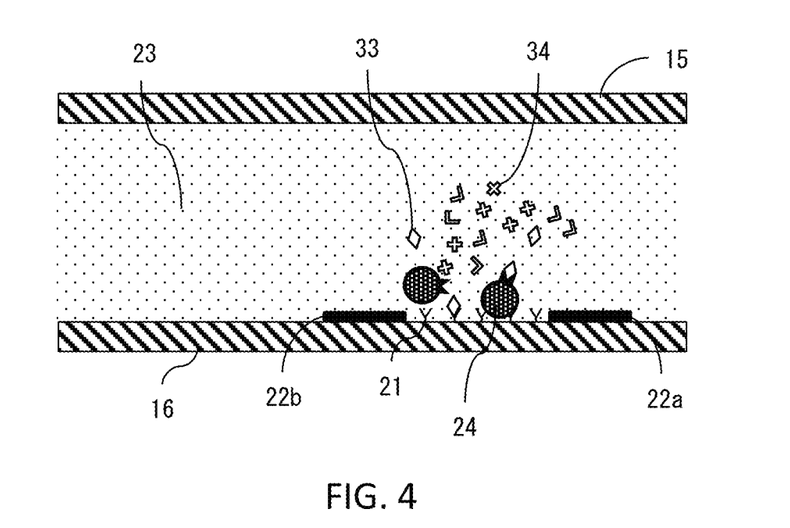
FIG. 4 shows, subsequently to FIG. 3, a schematic view of a step (c) included in the method according to the first embodiment.

In the step (c), as shown in FIG. 4, the bioparticles 26 aggregated in the step (b) are broken. As a result, the analyte 33 is released to the solution 23. Since the bioparticles 26 also contain substances 34 other than the analyte 33, the substances 34 are also released to the solution 23 after the breaking.

Figure 12:
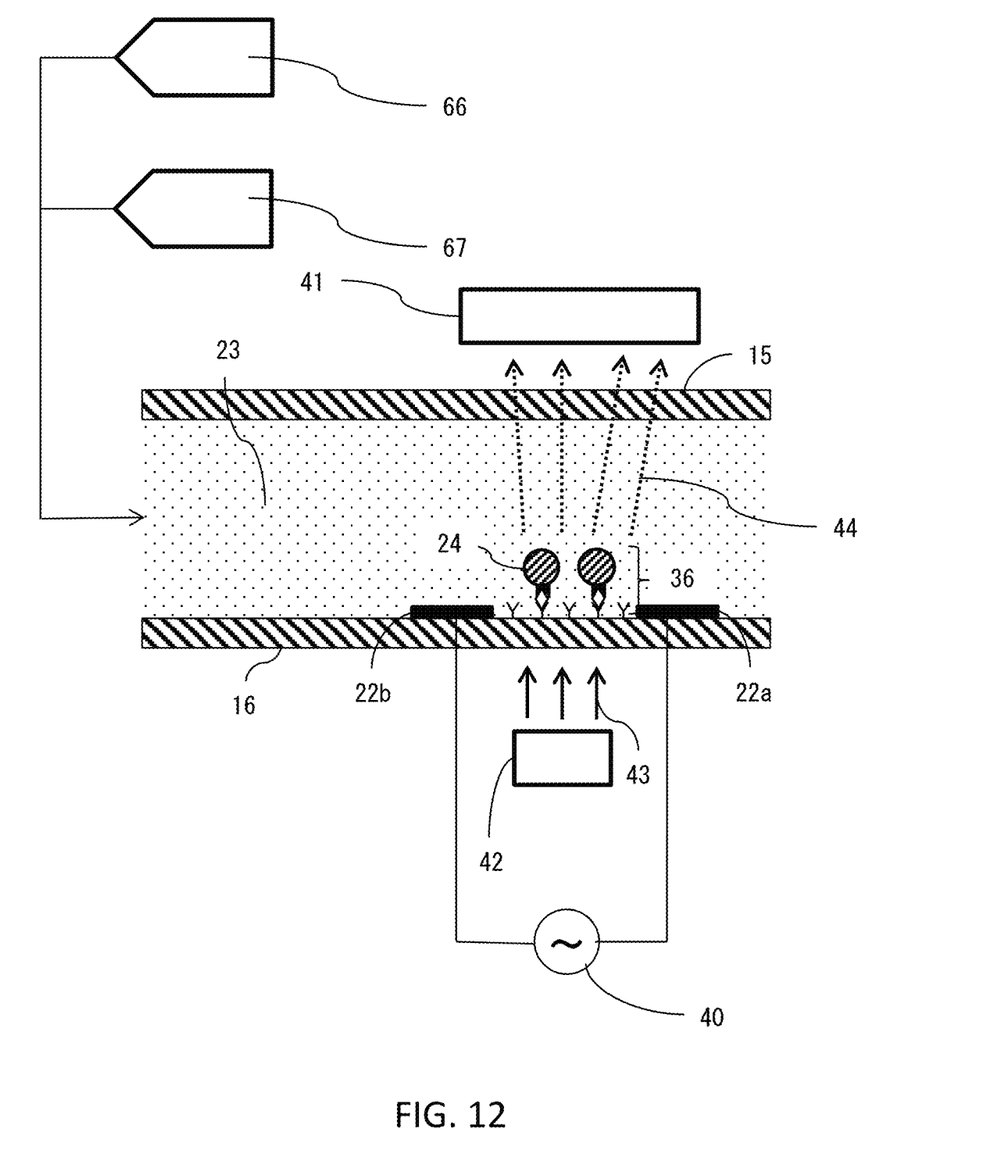
FIG. 12 shows a schematic view of a device for detecting an analyte in a case where bioparticles are broken chemically.
Figure 13:
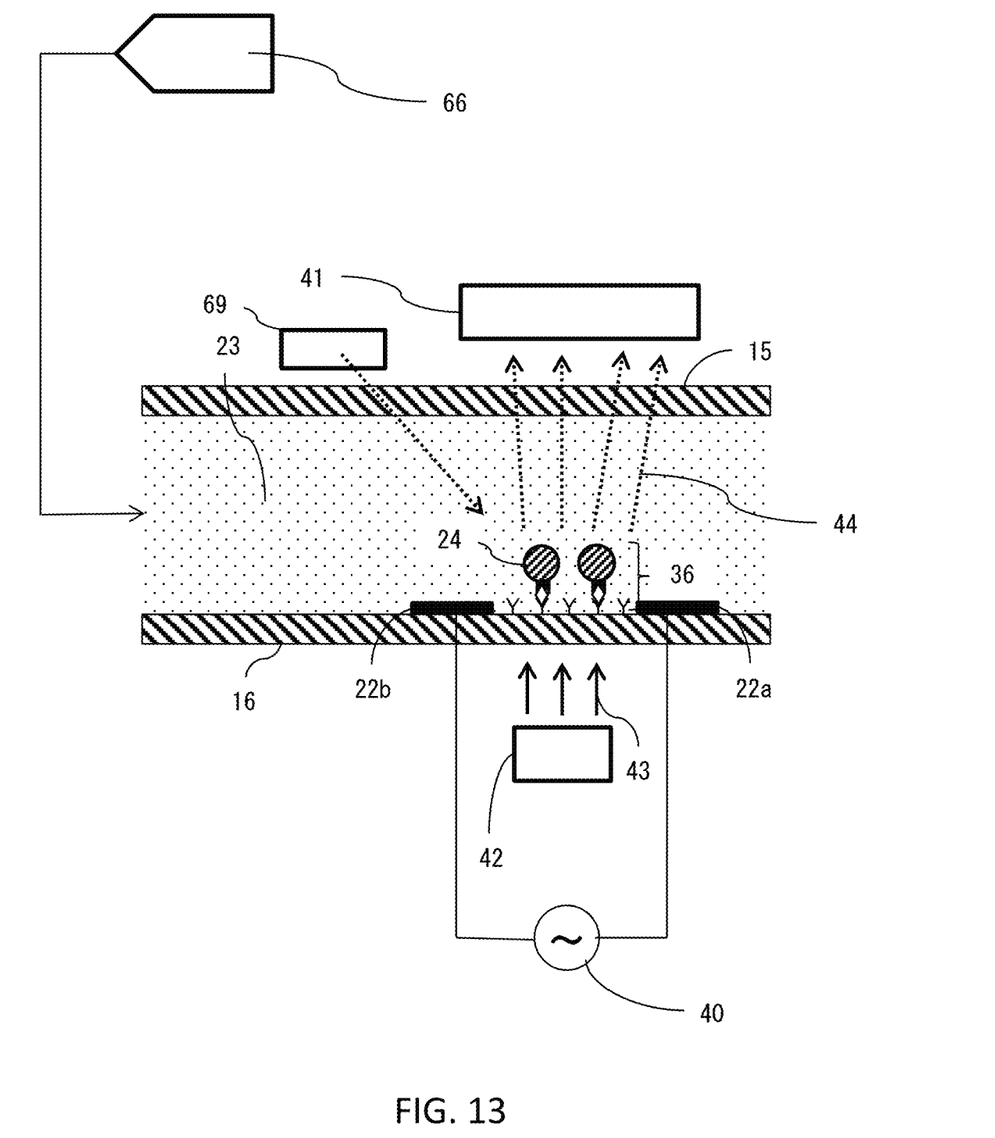
FIG. 13 shows a schematic view of a device for detecting an analyte in a case where bioparticles are broken physically.

A method for breaking the bioparticles 26 is roughly divided into a physical method and a chemical method. An example of the physical method is to heat the solution 23, to apply an ultrasonic wave to the bioparticles 26, or to apply a high voltage pulse to the bioparticles 26. An example of the chemical method is to add a bacteriolysis agent to the solution 23, to change the salt concentration of the solution 23, or to change the pH of the solution 23. It is desirable to apply a high voltage pulse to the bioparticles 26. When the chemical method is used, as shown in FIG. 12, a device for detecting the analyte according to the present embodiment may comprise not only the substrate 16, the alternating-current power supply 40, and a detector 41 (which will be described later), but also a solution supplying part 66 and a resolvent supplying part 67. The solution 23 is supplied from the solution supplying part 66 onto the substrate 16. A resolvent such as a bacteriolysis agent, a salt, an acid, or an alkali is supplied onto the substrate 16 from the resolvent supplying part 67. An example of the solution supplying part 66 is a syringe. An example of the resolvent supplying part 67 is also a syringe. The solution supplying part 66 may comprise a valve. The resolvent supplying part 67 may also comprise a valve. When the physical method is used, as shown in FIG. 13, a device for detecting the analyte according to the present embodiment may comprise not only the substrate 16, the alternating-current power supply 40, and the detector 41 (which will be described later), but also the solution supplying part 66 and a breaker 69. An example of the breaker 69 is a heater, an ultrasonic wave generator, or a high-voltage pulse generator. The alternating-current power supply 40 may double as a heater and a high-voltage pulse generator. The device for detecting the analyte according to the present embodiment may comprise a controller (not shown). The controller transmits a control signal to the alternating-current power supply 40, the detector 41, a light source 42 (which will be described later), the solution supplying part 66 and the resolvent supplying part 67 (or the breaker 69) in accordance with the method for detecting the analyte according to the present embodiment. The valves included in the solution supplying part 66 and the resolvent supplying part 67 may be controlled by the controller.

Figure 5:
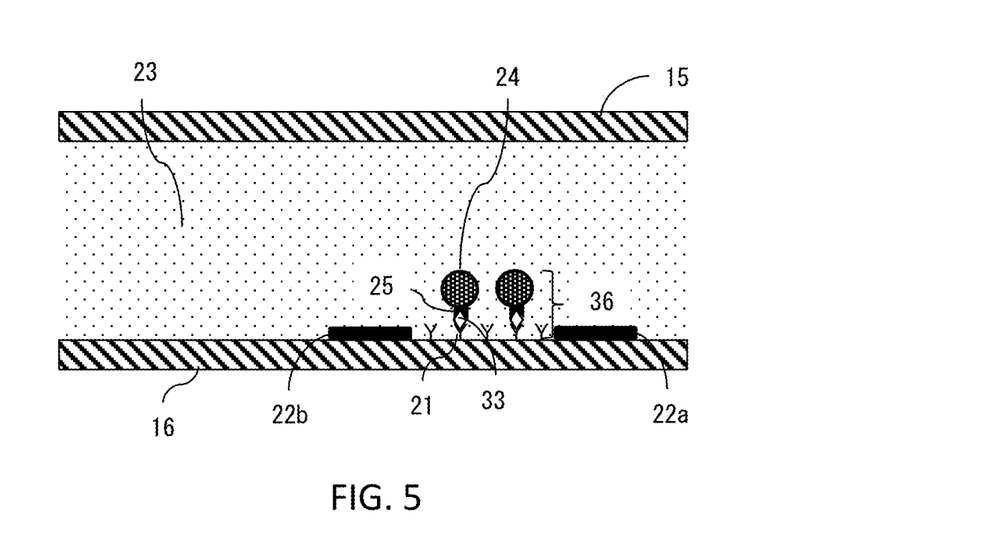
FIG. 5 shows a schematic view after completion of the step (c).

As shown in FIG. 5, the released analyte 33 is bound to both of the first antibody 21 and the second antibody 25. In this way, a sandwich structure 36 composed of the first antibody 21, the analyte 33 and the second antibody 25 is formed. Since the dielectric particles 24 having the second antibodies 25 are located with high density on the surface of the substrate 16 between the first electrode 22a and the second electrode 22b, the sandwich structures 36 are also formed with high density. Needless to say, the analyte 33 is located between the first antibody 21 and the second antibody 25. The dielectric particles 24 are immobilized onto the substrate 16 through the sandwich structure 36.

During the period between the end of the step (b) and the end of the step (c), it is desirable that the solution 23 remains in the flow path 12 so as not to flow through the flow path 12. In other words, it is desirable that the solution 23 has a flow rate of approximately 0 cm/minute. When the solution 23 flows through the flow path 12, the analyte 33 released from the bioparticles 26 would flow with the solution 23 through the flow path 12 without being bound to the first antibody 21.

(Step (d))

The step (d) is conducted after the step (c).

Figure 6:
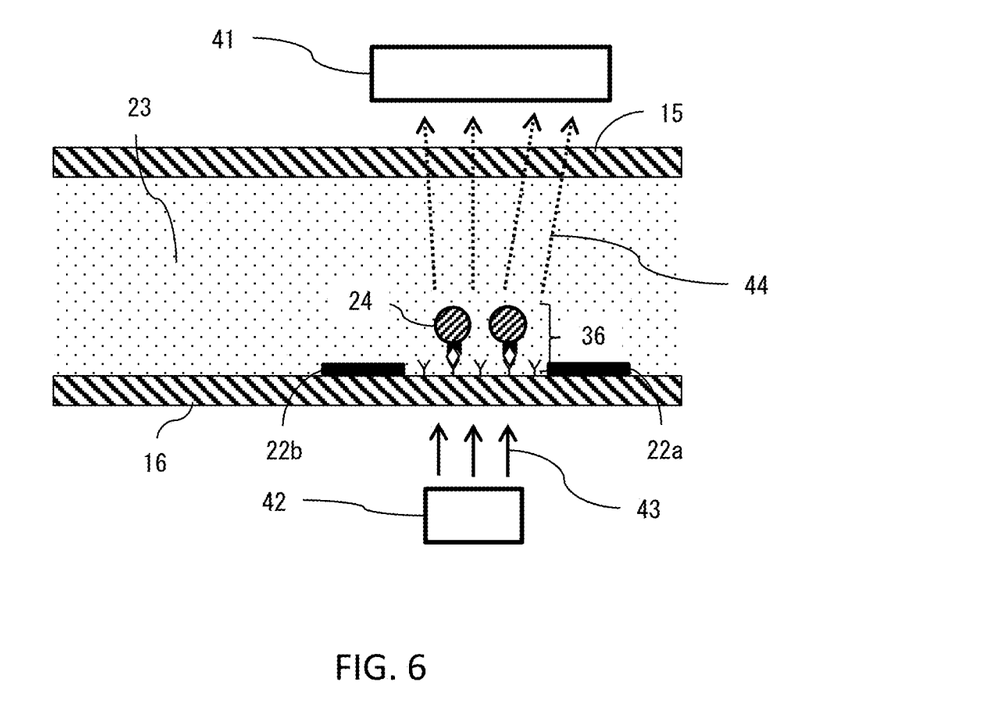
FIG. 6 shows, subsequently to FIG. 5, a schematic view of a step (d) included in the method according to the first embodiment.

As shown in FIG. 6, excited light 43 emitted from a light source 42 travels through the sandwich structure 36 to excite the fluorescent substance contained in the dielectric particles 24. In this way, fluorescent light 44 is emitted from the dielectric particles 24. This fluorescent light 44 is received by the detector 41. As just described, the analyte 33 is detected. Since the sandwich structures 36 are formed with high density, the analyte 33 is detected with high sensitivity. It is desirable that the substances 34 other than the analyte 33 are removed after the step (c) and before the step (d).

Second Embodiment

Next, the second embodiment of the present invention will be described.

The difference of the second embodiment from the first embodiment will be listed below.

(I) The substrate 16 has the first electrode 22a; however, the cover 15 has the second electrode 22b.

(II) The substrate 16 has the first antibodies 21 on the surface thereof near the first electrode 22a.

Figure 7:
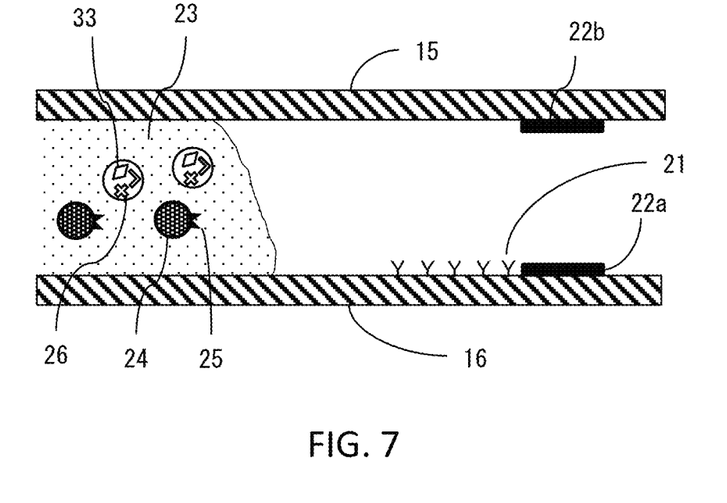
FIG. 7 shows a schematic view of a step (a) included in a method according to a second embodiment of the present invention.

See FIG. 7. Desirably, the substrate 16 has the first antibodies 21 on the surface of at least a part of the circumference of the first electrode 22a. More desirably, the first antibodies 21 are adjacent to the first electrode 22a. In the second embodiment, the bioparticles 26 and the dielectric particles 24, both of which have been dispersed in the solution 23, are located near the first electrode 22a on the surface of the substrate 16 with high density.

INDUSTRIAL APPLICABILITY

The present invention can be used for a device for collecting or detecting a virus.

REFERENTIAL SIGNS LIST

12 Flow path
15 Cover
16 Substrate
21 First antibody
22a First electrode
22b Second electrode
23 Solution
24 Dielectric particle
25 Second antibody
26 Bioparticle
33 Analyte
34 Substance other than analyte 33
36 Sandwich structure
40 Alternating-current power supply
41 Detector
42 Light source
43 Excited light
44 Fluorescent light
66 Solution supplying part
67 Resolvent supplying part
69 Breaker

The invention claimed is:

1. A method for detecting an analyte, the method comprising:

(a) supplying a solution onto a substrate comprising a first electrode and a second electrode;

wherein the substrate has a first antibody on the surface thereof between the first electrode and the second electrode;

the solution contains dielectric particles and at least one kind of bioparticles selected from the group consisting of viruses and cells;

each of the dielectric particles has a second antibody on the surface thereof;

each of the dielectric particles contains a fluorescent substance;

each of the bioparticles contains the analyte;

the first antibody is capable of binding to the analyte; and the second antibody is capable of binding to the analyte;

(b) drawing the bioparticles and the dielectric particles by dielectrophoresis to aggregate the bioparticles and the dielectric particles onto the surface of the substrate between the first electrode and the second electrode, both of which are comprised by the substrate, by applying an alternating voltage between the first electrode and the second electrode;

(c) breaking the bioparticles aggregated in the step (b) to release the analyte contained in the bioparticles;
wherein
the released analyte is bound to the first antibody and the second antibody to cause the dielectric particles to be immobilized onto the substrate through formation of a sandwich structure composed of the first antibody, the analyte, and the second antibody; and
(d) detecting the analyte through the fluorescent substance contained in the immobilized dielectric particles.

2. A method for detecting an analyte, the method comprising:
(a) supplying a solution to a flow path formed between a substrate comprising a first electrode and a cover comprising a second electrode;
wherein
the substrate has a first antibody on the surface thereof near the first electrode;
the solution contains dielectric particles and at least one kind of bioparticles selected from the group consisting of viruses and cells;
each of the dielectric particles has a second antibody on the surface thereof;
each of the dielectric particles contains a fluorescent substance;
each of the bioparticles contains the analyte;
the first antibody is capable of binding to the analyte; and
the second antibody is capable of binding to the analyte;
(b) drawing the bioparticles and the dielectric particles by dielectrophoresis to aggregate the bioparticles and the dielectric particles onto the surface of the substrate near the first electrode, which is comprised by the substrate, by applying an alternating voltage between the first electrode and the second electrode, which is comprised by the cover;
(c) breaking the bioparticles aggregated in the step (b) to release the analyte contained in the bioparticles;
wherein
the released analyte is bound to the first antibody and the second antibody to cause the dielectric particles to be immobilized onto the substrate through formation of a sandwich structure composed of the first antibody, the analyte, and the second antibody; and
(d) detecting the analyte through the fluorescent substance contained in the immobilized dielectric particles.

\* \* \* \* \*

UNITED STATES PATENT AND TRADEMARK OFFICE
CERTIFICATE OF CORRECTION

PATENT NO. : 10,684,254 B2  
APPLICATION NO. : 15/366143  
DATED : June 16, 2020  
INVENTOR(S) : Yasuaki Okumura et al.

Page 1 of 1

It is certified that error appears in the above-identified patent and that said Letters Patent is hereby corrected as shown below:

On the Title Page

Please add the following data:  
(30) Foreign Application Priority Data  
February 8, 2016    (JP)    2016-021421

Signed and Sealed this  
Twenty-third Day of March, 2021

Drew Hirshfeld  
*Performing the Functions and Duties of the  
Under Secretary of Commerce for Intellectual Property and  
Director of the United States Patent and Trademark Office*